(12) United States Patent
Kobayashi et al.

(10) Patent No.: US 11,150,863 B2
(45) Date of Patent: Oct. 19, 2021

(54) VEHICLE SOUND OUTPUT DEVICE, SOUND OUTPUT CONTROL METHOD, AND NON-TRANSITORY COMPUTER READABLE MEDIUM STORING SOUND OUTPUT CONTROL PROGRAM

(71) Applicant: Toyota Jidosha Kabushiki Kaisha, Toyota (JP)

(72) Inventors: Hideki Kobayashi, Miyoshi (JP); Akihiro Muguruma, Nagoya (JP); Yukiya Sugiyama, Toyota (JP); Shota Higashihara, Chiryu (JP); Riho Matsuo, Nagoya (JP); Naoki Yamamuro, Nagoya (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 0 days.

(21) Appl. No.: 16/231,677

(22) Filed: Dec. 24, 2018

(65) Prior Publication Data

US 2019/0212969 A1    Jul. 11, 2019

(30) Foreign Application Priority Data

Jan. 11, 2018    (JP) .............................. JP2018-002919

(51) Int. Cl.
*G06F 17/00*    (2019.01)
*G06F 3/16*    (2006.01)
(Continued)

(52) U.S. Cl.
CPC .............. *G06F 3/16* (2013.01); *A61B 5/0022* (2013.01); *A61B 5/18* (2013.01); *A61B 5/6893* (2013.01);
(Continued)

(58) Field of Classification Search
CPC . G06F 3/16; G06F 16/436; A61B 5/18; A61B 5/7405; A61B 5/0022;
(Continued)

(56) References Cited

U.S. PATENT DOCUMENTS 5,786,765 A * 7/1998 Kumakura ............. G08B 21/06
340/576
6,236,968 B1 * 5/2001 Kanevsky ............... G10L 17/26
704/275
(Continued)

FOREIGN PATENT DOCUMENTS

CN    101123027 A    2/2008
CN    10655653 A    4/2017
(Continued)

*Primary Examiner* — Joseph Saunders, Jr.
(74) *Attorney, Agent, or Firm* — Dinsmore & Shohl LLP

(57) ABSTRACT

A vehicle sound output device including: an acquiring section configured to acquire wakefulness level information that indicates a degree of a wakefulness state of a driver of a vehicle; and a control section configured to, in a case in which the degree of the wakefulness state indicates a decreased level of wakefulness, control a sound output section to output a sound based on at least one of a predetermined frequency, a predetermined tone, or a predetermined content that stimulates a sympathetic nerve of the driver.

15 Claims, 7 Drawing Sheets

| WAKEFULNESS LEVEL | FREQUENCY | TONE (DEVIATION DEGREE) | CONTENT |
|---|---|---|---|
| 9 | EVERY x1 MINUTES | NO CHANGE | CATEGORY 1 |
| 8 | EVERY x2 MINUTES (x1 > x2) | 1 | CATEGORY 2 |
| 7 | EVERY x3 MINUTES (x2 > x3) | 2 | CATEGORY 3 |
| ... | ... | ... | ... |

WAKEFULNESS LEVEL HIGH ↕ LOW

(51) Int. Cl.
*A61B 5/00* (2006.01)
*A61B 5/18* (2006.01)
*B60K 28/06* (2006.01)
*G08B 21/06* (2006.01)

(52) U.S. Cl.
CPC .......... *A61B 5/7203* (2013.01); *A61B 5/7405* (2013.01); *A61B 5/746* (2013.01); *B60K 28/06* (2013.01); *G08B 21/06* (2013.01); *A61B 5/0077* (2013.01); *A61B 2503/22* (2013.01)

(58) Field of Classification Search
CPC ..... A61B 5/6893; A61B 5/7203; A61B 5/746; A61B 5/0077; A61B 2503/22; B60K 28/06; G08B 21/06; G10L 17/00
See application file for complete search history.

(56) References Cited

U.S. PATENT DOCUMENTS

| | | | | |
|---|---|---|---|---|
| 8,108,083 | B2* | 1/2012 | Kameyama | G06F 16/48 701/1 |
| 8,185,380 | B2* | 5/2012 | Kameyama | G08G 1/0962 704/10 |
| 8,190,434 | B2* | 5/2012 | Kameyama | G10L 15/22 704/270 |
| 2008/0180257 | A1* | 7/2008 | Omi | G08B 21/06 340/575 |
| 2008/0218359 | A1* | 9/2008 | Ishida | G06K 9/00281 340/575 |
| 2011/0288424 | A1* | 11/2011 | Kanai | A61B 5/18 600/500 |
| 2012/0075122 | A1* | 3/2012 | Whitlow | A61B 5/18 340/963 |
| 2013/0093603 | A1* | 4/2013 | Tschirhart | A61B 5/18 340/902 |
| 2013/0325478 | A1* | 12/2013 | Matsumoto | B60W 50/08 704/274 |
| 2014/0104064 | A1* | 4/2014 | Nakai | G08B 21/06 340/575 |
| 2014/0167968 | A1* | 6/2014 | Tuzsuzov | B60K 28/066 340/576 |
| 2014/0276112 | A1* | 9/2014 | Fung | A61B 5/024 600/479 |
| 2015/0092056 | A1* | 4/2015 | Rau | G08G 1/167 348/148 |
| 2016/0180853 | A1 | 6/2016 | VanLund et al. | |
| 2016/0196105 | A1* | 7/2016 | Vartakavi | G06F 3/165 700/94 |
| 2017/0080856 | A1 | 3/2017 | Enomoto et al. | |
| 2017/0083285 | A1 | 3/2017 | Meyers et al. | |

FOREIGN PATENT DOCUMENTS

| | | |
|---|---|---|
| JP | 2007-206522 A | 8/2007 |
| JP | 2007-241535 A | 9/2007 |
| JP | 2009-143309 A | 7/2009 |
| JP | 2017-59043 A | 3/2017 |
| JP | 2017-084071 A | 5/2017 |

* cited by examiner

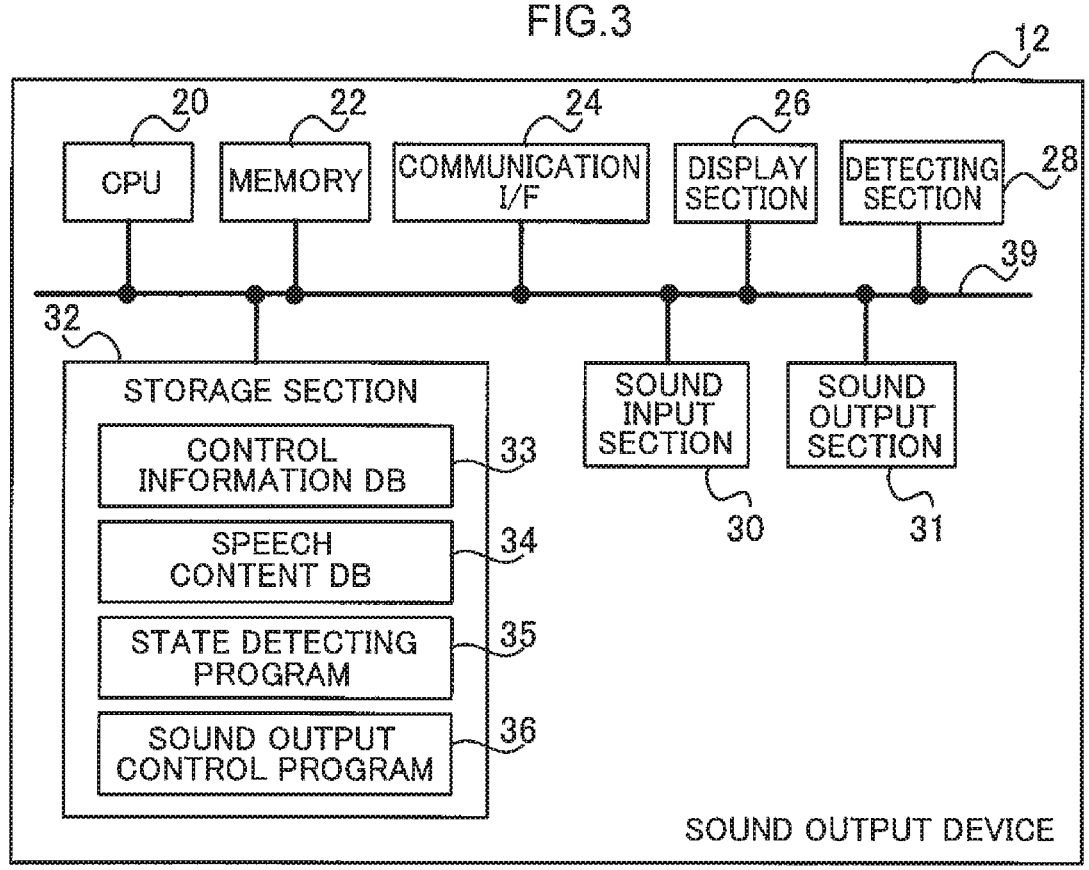

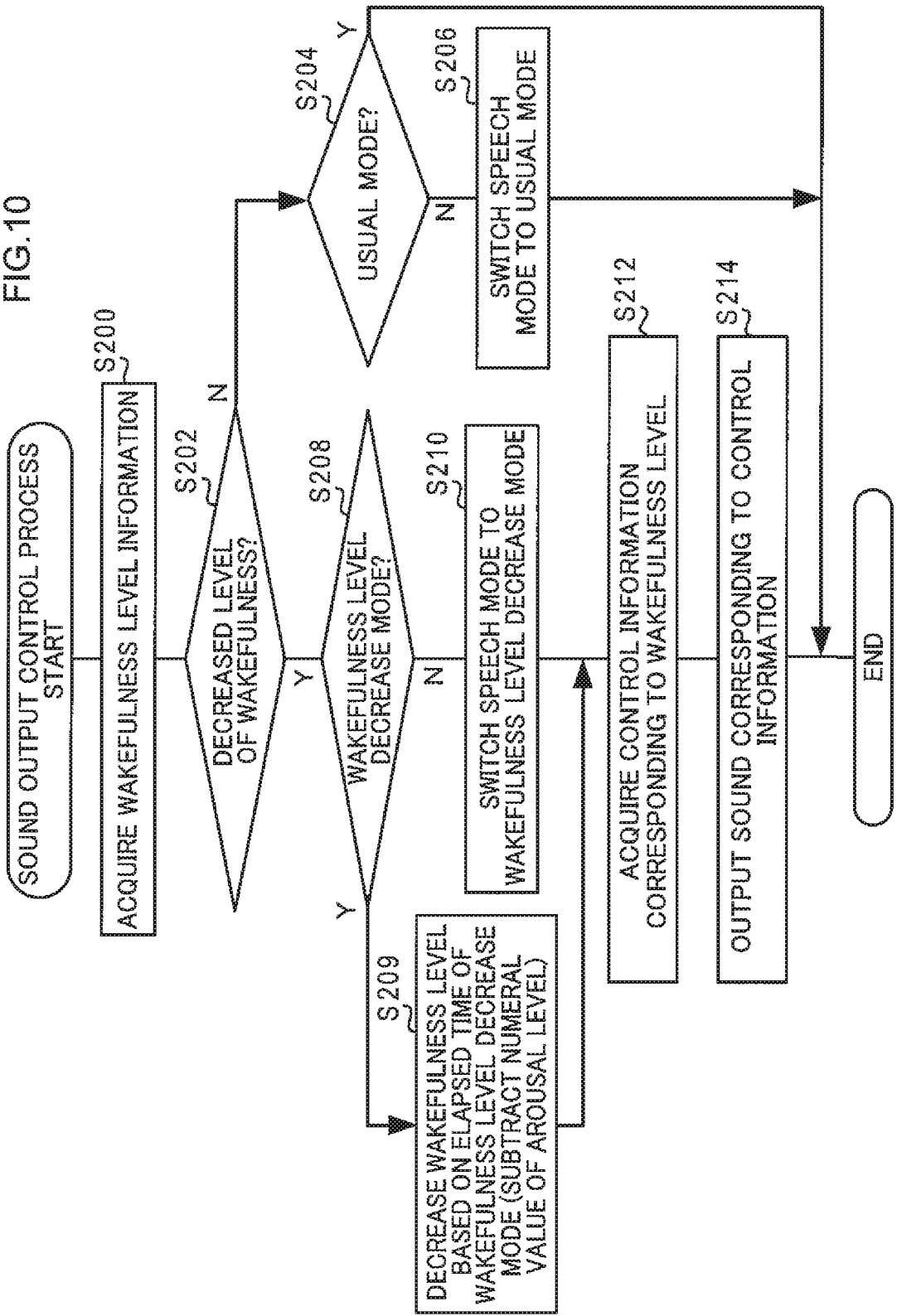

VEHICLE SOUND OUTPUT DEVICE, SOUND OUTPUT CONTROL METHOD, AND NON-TRANSITORY COMPUTER READABLE MEDIUM STORING SOUND OUTPUT CONTROL PROGRAM

CROSS-REFERENCE TO RELATED APPLICATION

This application claims priority under 35 USC 119 from Japanese Patent Application No. 2018-002919, filed on Jan. 11, 2018, the disclosure of which is incorporated by reference herein.

BACKGROUND

Technical Field

The present disclosure relates to a vehicle sound output device, a sound output control method, and a non-transitory computer readable medium storing a sound output control program.

Related Art

Japanese Patent Application Laid-Open (JP-A) No. 2007-241535 discloses an agent device that makes conversation with a user through an agent so that a user feels a sense of closeness. JP-A No. 2007-241535 discloses a technique of synthesizing and outputting sounds (voice) having contents for urging the user to have a conversation, in a case in which a time from detection of an input sound data to detection of the next sound data exceeds a predetermined time.

In the technique described in JP-A No. 2007-241535, only the conversation is made with the user so that the user feels the sense of closeness, and a decrease in a wakefulness level of the user during driving is not considered. For this reason, even though a sound output device such as an artificial intelligence (AI) speaker to which the technique described in JP-A No. 2007-241535 is applied is mounted in a vehicle, it is not possible to effectively suppress a decrease in a wakefulness level of a driver.

SUMMARY

The disclosure provides a vehicle sound output device, a sound output control method, and a non-transitory computer readable medium storing a sound output control program that may suppress a decrease in an wakefulness level of a driver.

A first aspect of the present disclosure is a vehicle sound output device including: an acquiring section configured to acquire wakefulness level information that indicates a degree of a wakefulness state of a driver of a vehicle; and a control section configured to, in a case in which the degree of the wakefulness state indicates a decreased level of wakefulness, control a sound output section to output a sound based on at least one of a predetermined frequency, a predetermined tone, or a predetermined content that stimulates a sympathetic nerve of the driver.

According to the vehicle sound output device of the first aspect, since all of the frequency, the tone, and the content of the output sound stimulates the sympathetic nerve of the driver, who is a listener, the sympathetic nerve of the driver may be activated. Generally, in a state in which the sympathetic nerve is activated, a wakefulness level tends to become high. Therefore, the vehicle sound output device of the first aspect may suppress a decrease in the wakefulness level of the driver.

The "tone" of the sound for stimulating the sympathetic nerve refers to a rhythm or an intonation of the entire speech and a rhythm and an intonation at the time of speaking a word. Specific examples of the "tone" may include a tempo, an intonation, or the like, of the speech.

According to a second aspect of the present disclosure, in the first aspect, the predetermined frequency may increase as the degree of the wakefulness state decreases.

According to the vehicle sound output device of the second aspect, the sound is output to the driver more frequently as the degree of the wakefulness state becomes lower. Accordingly, the second aspect of the present disclosure may stimulate the sympathetic nerve of the driver based on the degree of the wakefulness state.

According to a third aspect of the present disclosure, in the above aspect, the predetermined frequency may increase as a duration of the decreased level of wakefulness increases.

According to the vehicle sound output device of the third aspect, the sound is more frequently output to the drive as the duration of the decreased level of wakefulness becomes longer. Accordingly, the third aspect of the present disclosure may rapidly increase the wakefulness level of the driver, for example, even in a case in which the wakefulness level is difficult to be increased.

According to a fourth aspect of the present disclosure, in the above aspect, the predetermined tone may have a deviation degree that increases as the degree of the wakefulness state decreases.

According to the vehicle sound output device of the fourth aspect, a sound with further deviated tone is output to the driver as the degree of the wakefulness state decreases. Accordingly, the fourth aspect of the present disclosure may stimulate the sympathetic nerve of the driver based on the degree of the wakefulness state.

According to a fifth aspect of the present disclosure, in the above aspect, the predetermined tone may have a deviation degree that increases as a duration of the decreased level of wakefulness increases.

According to the vehicle sound output device of the fifth aspect, a sound with further deviated tone is output to the driver as the duration of the decreased level of wakefulness becomes longer. Accordingly, the fifth aspect of the present disclosure may rapidly increase the wakefulness level of the driver, for example, even in a case in which the wakefulness level is difficult to be increased.

According to a sixth aspect of the present disclosure, in the above aspect, the predetermined content may cause an interest degree of the driver to increase as the degree of the wakefulness state decreases.

According to the vehicle sound output device of the sixth aspect, a sound including a content in which the interest degree of the driver is increased is output as the degree of the wakefulness state decreases. Accordingly, the sixth aspect of the present disclosure may stimulate the sympathetic nerve of the driver based on the degree of the wakefulness state.

According to a seventh aspect of the present disclosure, in the above aspect, the predetermined content may cause an interest degree of the driver to increase as a duration of the decreased level of wakefulness increases.

According to the vehicle sound output device of the seventh aspect, a sound including a content in which the interest degree of the driver is increased is output as the duration of the decreased level of wakefulness becomes longer. Accordingly, the seventh aspect of the present disclosure may rapidly increase the wakefulness level of the driver, for example, even in a case in which the wakefulness level is difficult to be increased.

An eighth aspect of the present disclosure is a sound output control method including: acquiring wakefulness level information that indicates a degree of a wakefulness state of a driver of a vehicle; and in a case in which the degree of the wakefulness state indicates a decreased level of wakefulness, controlling a sound output section to output a sound based on at least one of a predetermined frequency, a predetermined tone, and a predetermined content that stimulates a sympathetic nerve of the driver.

According to the sound output control method of the eighth aspect, as in the first aspect, since all of the frequency, the tone, and the content of the output sound stimulate the sympathetic nerve of the driver, who is a listener, the sympathetic nerve of the driver may be activated. Therefore, the sound output control method according to the eighth aspect may suppress a decrease in the wakefulness level of the driver.

A ninth aspect of the present disclosure is a non-transitory computer readable medium storing a sound output control program causing a computer to execute a process, the process including: acquiring wakefulness level information that indicates a degree of a wakefulness state of a driver of a vehicle; and in a case in which the degree of the wakefulness state indicates a decreased level of wakefulness, controlling a sound output section to output a sound based on at least one of a predetermined frequency, a predetermined tone, and a predetermined content that stimulates a sympathetic nerve of the driver.

According to the sound output control program of the ninth aspect, as in the first aspect, since all of the frequency, the tone, and the content of the output sound stimulate the sympathetic nerve of the driver, who is a listener, the sympathetic nerve of the driver may be activated. Therefore, the sound output control program according to the ninth aspect may suppress a decrease in the wakefulness level of the driver.

According to the above aspects, the present disclosure may provide a vehicle sound output device, a sound output control method, and a non-transitory computer readable medium storing a sound output control program that may suppress a decrease in an wakefulness level of a driver.

BRIEF DESCRIPTION OF THE DRAWINGS

Exemplary embodiments will be described in detail based on the following figures, wherein:

FIG. 3 is a block diagram showing a hardware configuration of a sound output device according to the first exemplary embodiment;

FIG. 4 is a diagram showing a control information database according to the first exemplary embodiment;

FIG. 10 is a flowchart showing a sound output control process executed by a sound output device according to a second exemplary embodiment.

DETAILED DESCRIPTION

Hereinafter, exemplary embodiments of the disclosure will be described in detail with reference to the drawings.

First Exemplary Embodiment

Figure 1:
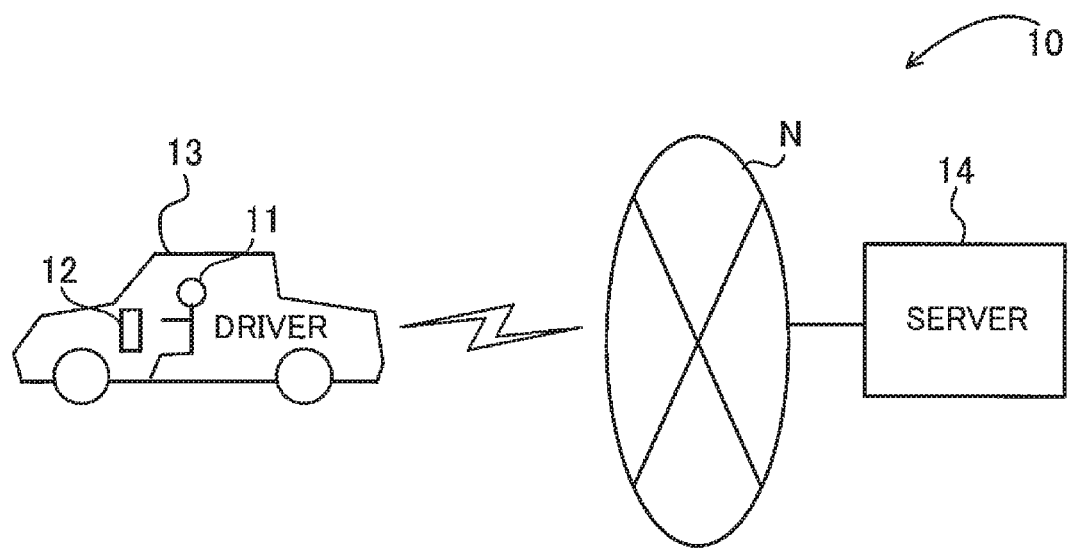
FIG. 1 is a diagram showing a configuration of a sound output system according to a first exemplary embodiment.

First, a configuration of a sound output system 10 according to the present exemplary embodiment will be described with reference to FIG. 1. As shown in FIG. 1, the sound output system 10 according to the present exemplary embodiment includes a sound output device 12 that accepts a speech by a driver 11 in a vehicle 13, executes an application corresponding to the accepted speech, and outputs an execution result as a sound. The sound output device 12 according to the present exemplary embodiment is mounted in advance in the vehicle 13, but may be brought from the outside into the vehicle 13 by the driver 11.

The sound output device 12 is connected to a network N by wireless communication. Further, a server 14 is connected to the network N. Therefore, the sound output device 12 and the server 14 can communicate with each other through the network N.

Next, hardware configurations of the sound output device 12 and the server 14 will be described.

First, a hardware configuration of the server 14 will be described with reference to FIG. 2. Examples of the server 14 according to the present exemplary embodiment can include a server computer such as a so-called cloud server.

Figure 2:
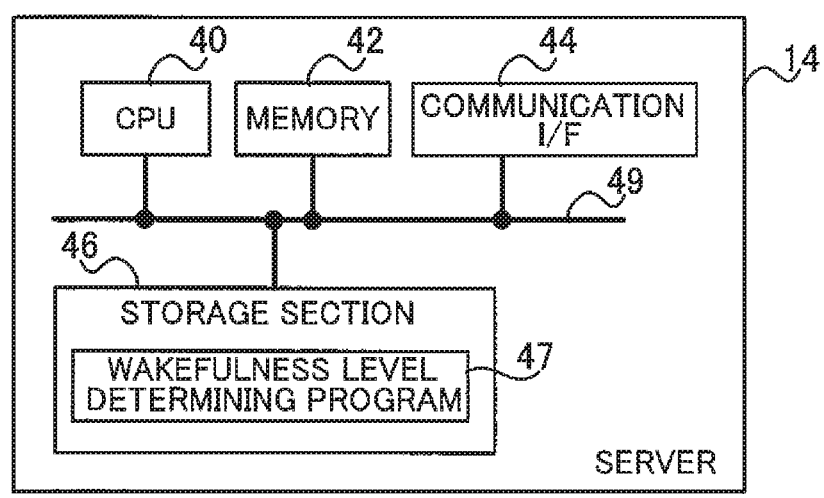
FIG. 2 is a block diagram showing a hardware configuration of a server according to the first exemplary embodiment.

As shown in FIG. 2, the server 14 includes a central processing unit (CPU) 40 and a memory 42 as a temporary storage area. Further, the server 14 includes a communication interface (I/F) 44 used at the time of performing communication with an external device, and a storage section 46 that is non-volatile. The CPU 40, the memory 42, the communication I/F 44, and the storage section 46 are connected to a bus 49.

The storage section 46 stores a wakefulness level determining program 47 for executing a wakefulness level determining process for determining a wakefulness level of the driver 11.

Next, a hardware configuration of the sound output device 12 will be described with reference to FIG. 3. Examples of the sound output device 12 according to the present exemplary embodiment can include an AI speaker, a smartphone, a mobile information terminal device, and the like.

As shown in FIG. 3, the sound output device 12 includes a CPU 20 and a memory 22 as a temporary storage area. Further, the sound output device 12 includes a communication I/F 24 used at the time of performing communication with an external device, a display section 26 such as a liquid crystal display, a sound input section 30 such as a microphone, a sound output section 31 outputting information by a sound such as a speaker, and a storage section 32 that is non-volatile. Further, the sound output device 12 includes a detecting section 28 such as a sensor for detecting a state of the driver 11. The "state" of the driver 11 detected by the detecting section 28 is information required for a state determining section 62 (see FIG. 6) (to be described in detail below) of the server 14 to determine the wakefulness level of the driver 11. Namely, the "state" of the driver 11 is information corresponding to a method for determining the wakefulness level by the state determining section 62.

Note that, in the present exemplary embodiment, a configuration in which the sound output device 12 includes the detecting section 28, is described. However, the detecting section 28 may be provided outside the sound output device 12. The CPU 20, the memory 22, the communication I/F 24, the display section 26, the detecting section 28, the sound input section 30, the sound output section 31, and the storage section 32 are connected to a bus 39.

The storage section 32 stores a control information database (DB) 33 and a speech content database (DB) 34. In FIG. 3, an example of the control information DB 33 is shown. As shown in FIG. 3, a frequency of the speech (hereinafter, simply referred to as a "frequency"), a tone of the speech (hereinafter, simply referred to as a "tone"), and a content of the speech (hereinafter, simply referred to as a "content") are stored as control information in the control information DB 33 in association with the wakefulness level of the driver 11. Note that, in the present exemplary embodiment, the smaller the number indicating a degree of a wakefulness state of the driver 11, the lower the wakefulness level of the driver 11 is. In other words, the larger the number representing the wakefulness level, the more the driver 11 is awake. Although not shown in FIG. 4, in a case in which the wakefulness state of the driver 11 is a usual state (namely, in a case in which it is considered that the wakefulness level is not decreased), in the present exemplary embodiment, the wakefulness level is set to "10".

The "frequency" in the control information DB 33 is a frequency of the speech performed to the driver 11. In other words, "frequency" is a frequency in which the sound output device 12 talks to the driver 11. As illustrated in FIG. 4, in the present exemplary embodiment, the wakefulness level and the frequency of the speech are associated with each other, such that the frequency of the speech becomes greater by talking to the driver more frequently (interval of speech decreases), as the wakefulness level decreases. In general, as the sound output device talks to the driver 11 more frequently, stimulation of a sympathetic nerve of the driver 11 can be expected. Therefore, in the present exemplary embodiment, as the wakefulness level becomes lower, the frequency of the speech becomes greater to stimulate the sympathetic nerve of the driver 11.

Further, the "tone" in the control information DB 33 is a tone of the speech performed to the driver 11. The "tone" refers to a rhythm or an intonation of the entire speech and a rhythm and an intonation at the time of speaking a word. Specific examples of the "tone" can include a tempo, an intonation, or the like, of the speech. As shown in FIG. 4, "1" and "2" in the "tone" indicate a deviation degree of the tone, and the larger the number, the larger the deviation degree. As illustrated in FIG. 4, in the present exemplary embodiment, the wakefulness level and the deviation degree of the tone are associated with each other, such that the deviation degree of the tone is increased as the wakefulness level decreases. In general, as the tone of speech is deviated, stimulation of the sympathetic nerve of the driver 11 can be expected. Therefore, in the present exemplary embodiment, as the wakefulness level decreases, the deviation degree of the tone of the speech is increased so as to stimulate the sympathetic nerve of the driver 11.

Figure 5:
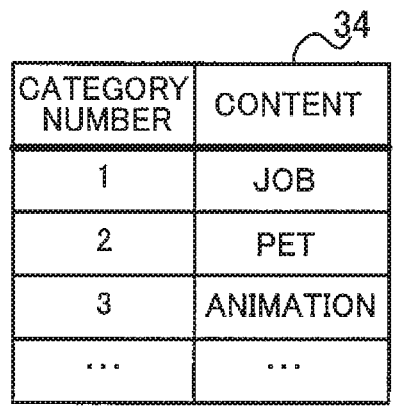
FIG. 5 is a diagram showing a speech content database according to the first exemplary embodiment.

Furthermore, the "content" in the control information DB 33 is a content for a topic of the speech performed to the driver 11. "Category 1" to "Category 3" in the "content" shown in FIG. 4 indicate contents of the speech, more specifically, kinds (categories) of topics in the speech. In the present exemplary embodiment, details of the categories in the content of the speech are managed by the speech content DB 34. In FIG. 5, an example of the speech content DB 34 is shown. As shown in FIG. 5, in the speech content DB 34, content information indicating the categories of the contents (the topics), and the like, is associated with category numbers. Note that in the present exemplary embodiment, the higher the interest degree of the driver 11 in the content (the category), in other words, the higher the interest of the driver 11 in the topic, the larger the value of a category number. For example, in the speech content DB 34 illustrated in FIG. 5, a topic in which an interest of the driver 11 is highest in Categories 1 to 3 is a topic relating to an "animation" of Category 3, and topics in which an interest of the driver 11 is sequentially decreased are topics relating to a "pet" of Category 2 and a "job" of Category 1. As illustrated in FIG. 4, in the present exemplary embodiment, the content and the wakefulness level are associated, such that the interest degree of the driver 11 in the content is increased as the wakefulness decreases. In general, as the interest in the topic increases, stimulation of the sympathetic nerve of the driver 11 can be expected. Therefore, in the present exemplary embodiment, as the wakefulness level decreases, the interest degree of a topic (a content) of the speech is increased so as to stimulate the sympathetic nerve of the driver 11.

A method of constructing the control information DB 33 is not particularly limited, and for example, the control information DB 33 can be configured in advance by an experiment, or the like. Further, a method of configuring the speech content DB 34 is also not particularly limited, and for example, the speech content DB 34 may be set in advance by the driver 11. Further, for example, a control section 50 of the sound output device 12 or the server 14 may monitor a speech content of the driver 11, count appearance frequencies of words representing the respective categories, and configure the speech content DB 34 with contents in which the driver 11 has an interest in a sequence of a category having a large count number.

The storage section 32 also stores a state detecting program 35 for executing a state detecting process (to be described in detail below) that detects the state of the driver 11 and a sound output control program 36 for executing a sound output control process (described in detail below) that control an output (a speech) of the sound, based on the wakefulness level of the driver 11.

Next, configurations of the sound output device 12 and the server 14 according to the present exemplary embodiment will be described with reference to FIG. 6.

Figure 6:
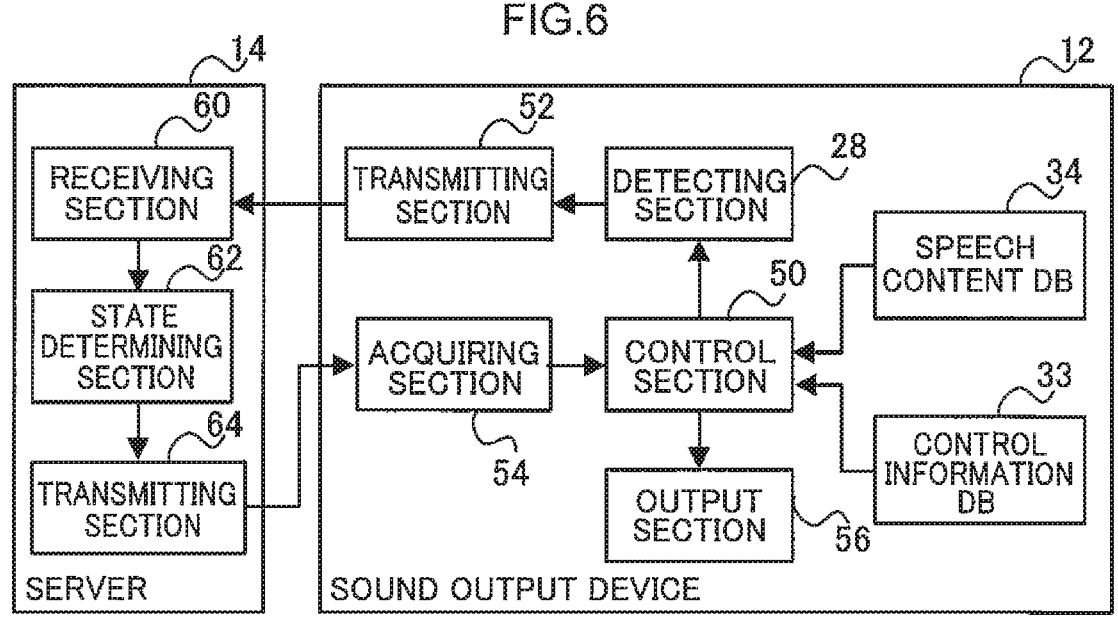
FIG. 6 is a block diagram showing functional configurations of the server and the sound output device according to the first exemplary embodiment.

As shown in FIG. 6, the server 14 includes a receiving section 60, a state determining section 62, and a transmitting section 64. The CPU 40 of the server 14 functions as the receiving section 60, the state determining section 62, and the transmitting section 64 by executing the wakefulness level determining program 47 stored in the storage section 46.

The receiving section 60 receives a detection result of the detecting section 28 from the sound output device 12 through the communication I/F 44. The state determining section 62 determines the wakefulness level of the driver 11 based on the detection result received by the receiving section 60. A method of determining the wakefulness level of the driver 11 by the state determining section 62 is not particularly limited. For example, it is generally known that the wakefulness level is decreased in a case in which a parasympathetic nerve is superior to the sympathetic nerve. Further, a method of determining the wakefulness level (whether or not the driver is drowsy) from an index of autonomic nerve activity is also known. For example, it is known that a low frequency (LF) obtained from time series data of heart rate variability mainly reflects activity of the sympathetic nerve of the autonomic nervous activity, and is also influenced by the parasympathetic nerve, and since a high frequency (HF) is influenced by only the parasympathetic nerve (a cardiac vagus nerve) of the autonomic nerve activity, it is used as an index of parasympathetic nerve activity. Further, for example, sympathetic nervous activity (SNA) (SNA=LF/HF) of which a value is increased in the case of an excited state or a tension state or parasympathetic nervous activity (PSNA) (PSNA=HF) of which a value is increased in the case of a relaxed state such as a rest state or a sleep state is known as an index of general autonomic nervous activity. Therefore, a sensor monitoring a heart rate of the driver 11 may be provided as the detecting section 28, a heart rate variability state of the driver 11 may be detected by the detecting section 28, and the state determining section 62 may acquire time series data of heart rate variability of the driver 11 as a detection result and determine the wakefulness level based on the index described above.

Further, it is generally known that eyelids tend to descend (be closed) as the wakefulness level is decreased. Further, a head tends to descend (fall) as the wakefulness level is decreased. Therefore, a camera capturing an image of a face (a head) of the driver 11 may be provided as the detecting section 28, and the state determining section 62 may acquire an image-capturing data as a detection result and determine the wakefulness level based on a descent degree of the eyelids, a descent degree of the head, or the like.

The transmitting section 64 transmits wakefulness level information indicating the wakefulness level, as a determining result of the state determining section 62 to the sound output device 12 through the communication I/F 44.

As shown in FIG. 6, the sound output device 12 includes a control section 50, a transmitting section 52, an acquiring section 54, and an output section 56. The CPU 20 of the sound output device 12 functions as the control section 50 and the transmitting section 52 shown in FIG. 6 by executing the state detecting program 35 stored in the storage section 32. Further, the CPU 20 of the sound output device 12 functions as the control section 50, the acquiring section 54, and the output section 56 by executing the sound output control program 36 stored in the storage section 32.

The control section 50 controls the detecting section 28 to detect the state of the driver 11 per first interval or second interval to be described in detail below. The transmitting section 52 transmits a detection result by the detecting section 28 to the server 14 through the communication I/F 24.

Further, the control section 50 acquires, by the acquiring section 54, the wakefulness level information from the server 14 through the communication I/F 24, and acquires the control information (specifically, the frequency, the tone, and the content) corresponding to the wakefulness level indicated by the acquired wakefulness level information from the control information DB 33 and the speech content DB 34.

Further, the control section 50 generates a speech data for performing a speech corresponding to the acquired control information, and outputs the speech data to the output section 56. The output section 56 allows a speech corresponding to the input speech data to be output from the sound output section 31. In the present exemplary embodiment, a speech mode in which the sound output device 12 outputs the speech (performs the speech) has two speech modes. The two speech modes are "a usual mode", and "a wakefulness level decrease mode" used in a case in which the wakefulness level is decreased. The speech mode is set to any one of the two speech modes. The usual mode is a speech mode for performing speech when responding to a speech from the driver 11, in the case of performing a predetermined navigation to the driver 11, or the like. The wakefulness level decrease mode is a mode for improving the wakefulness level of the driver 11 based on the wakefulness level of the driver 11, in other words, based on a decrease degree of the wakefulness level.

Next, operations of the sound output device 12 and the server 14 according to the present exemplary embodiment will be described.

Figure 7:
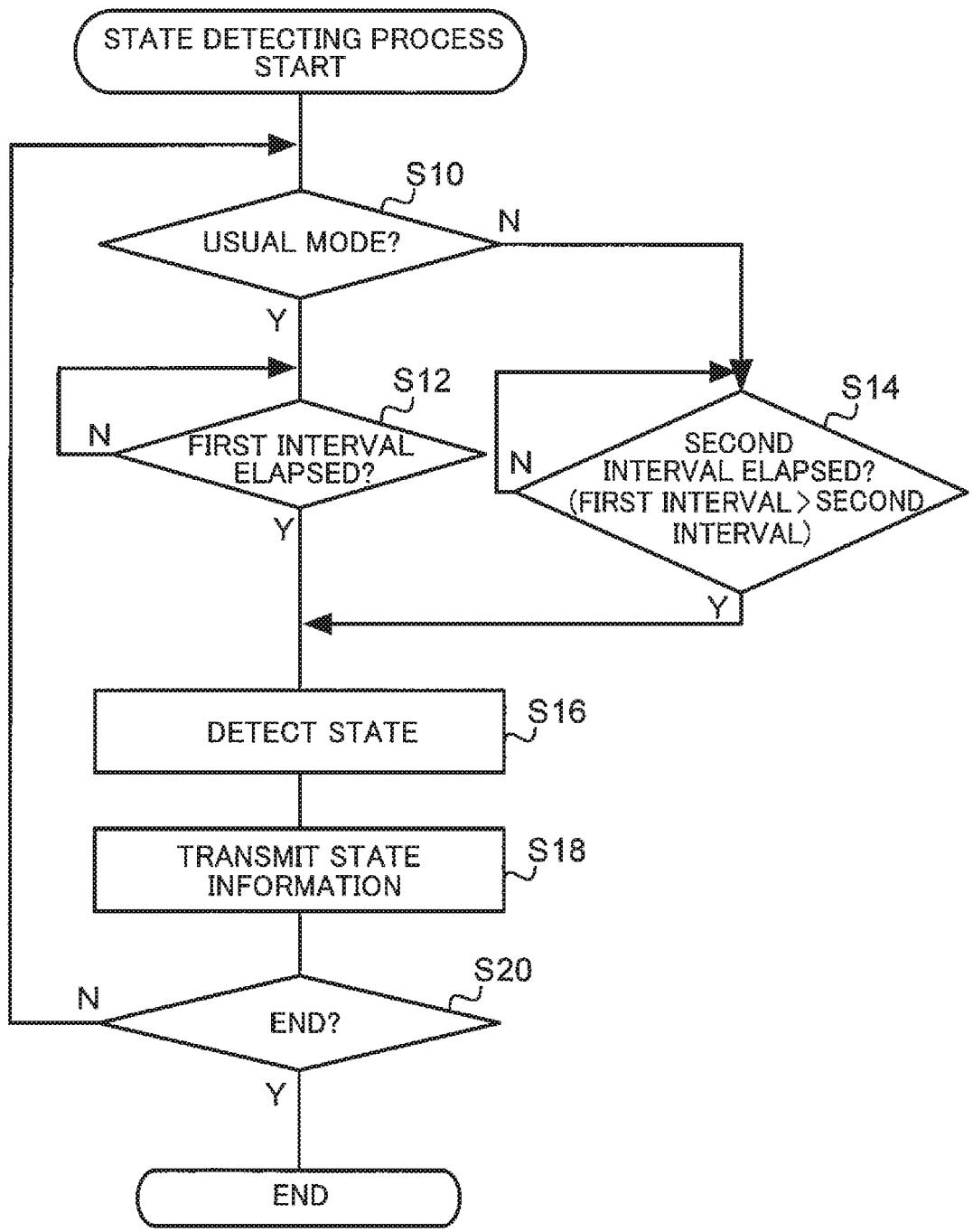
FIG. 7 is a flowchart showing a state detecting process executed by the sound output device according to the first exemplary embodiment.

First, as an operation of the sound output device 12, a state detecting process of detecting the state of the driver 11 will be described. FIG. 7 is a flowchart showing an example of a flow of the state detecting process executed by the CPU 20 of the sound output device 12 according to the present exemplary embodiment. Further, in the present exemplary embodiment, the state detecting process shown in FIG. 7 is executed by executing by the CPU 20, the state detecting program 35 stored in advance in the storage section 32. Further, the state detecting process shown in FIG. 7 is executed, for example, in a case in which an engine of the vehicle 13 is started.

In step S10 shown in FIG. 7, the control section 50 determines whether or not the speech mode of the speech output from the sound output section 31 by the output section 56 is the usual mode. In the present exemplary embodiment, immediately after the engine of the vehicle 13 is started (namely, immediately after the present state detecting process is executed) the speech mode is set to the usual mode. In a case in which the speech mode is set to the usual mode, an affirmative determination is made in step S10, and the process proceeds to step S12.

In step S12, the control section 50 determines whether or not the first interval has elapsed since last execution of step S16. Note that immediately after the present state detecting process is executed, it is determined whether or not the first interval has elapsed since the present state detecting process was executed. Until the first interval elapses, a negative determination is made in step S12. On the other hand, when the first interval elapses, an affirmative determination is made in step S12, and the process proceeds to step S16.

Meanwhile, in a case in which the set speech mode is the wakefulness level decrease mode, a negative determination is made in step S10, and the process proceeds to step S14. In step S14, the control section 50 determines whether or not the second interval has elapsed since last execution of step S16. Note that immediately after the present state detecting process is executed, it is determined whether or not the second interval has elapsed since the present state detecting process was executed. Until the second interval elapses, a negative determination is made in step S14. On the other hand, when the second interval elapses, an affirmative determination is made in step S14, and the process proceeds to step S16. The second interval is an interval shorter than the first interval, and the first interval and the second interval are predetermined.

In step S16, the control section 50 instructs the detecting section 28 to detect the state of the driver 11. The detecting section 28 detects the state of the driver 11 as described above, and outputs state information indicating a detection result to the transmitting section 52.

In the next step S18, the transmitting section 52 transmits the detection result input from the detecting section 28 to the server 14. The server 14 that has received the detection result executes a wakefulness level determining process, and transmits the wakefulness level information of the driver 11, determined based on the detection result, to the sound output device 12.

In the next step S20, the control section 50 determines whether or not to end the present state detecting process. For example, in a case in which a predetermined condition for ending the present state detecting process is satisfied, such as a case in which the engine of the vehicle 13 is stopped, an affirmative determination is made in step S20, and the present state detecting process ends. On the other hand, in a case in which the predetermined condition is not satisfied, a negative determination is made in step S20, and the process returns to step S10 and is repeated.

Figure 8:
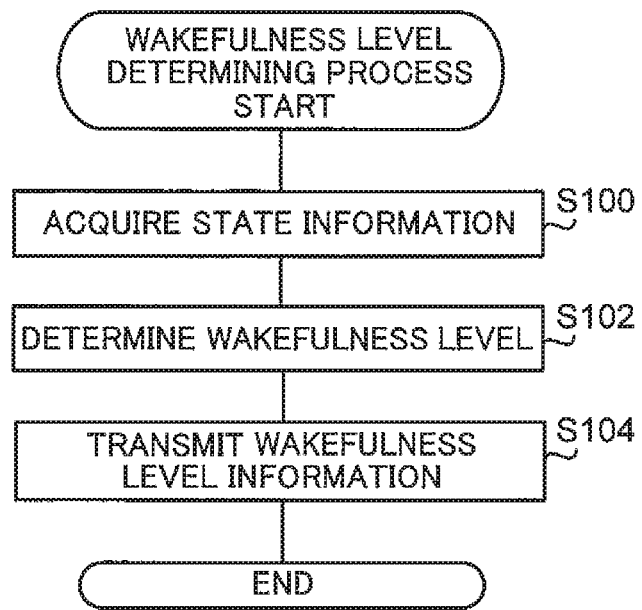
FIG. 8 is a flowchart showing a wakefulness level determining process executed by the server according to the first exemplary embodiment.

The state detecting process is executed in the sound output device 12, and the wakefulness level determining process as described above is executed in the server 14. Therefore, as an operation of the server 14, the wakefulness level determining process will be described. FIG. 8 is a flowchart showing an example of a flow of the wakefulness level determining process executed by the CPU 40 of the server 14 according to the present exemplary embodiment. Further, in the present exemplary embodiment, the wakefulness level determining process shown in FIG. 8 is executed by the CPU 40 by executing the wakefulness level determining program 47 stored in advance in the storage section 46.

In step S100 shown in FIG. 8, the receiving section 60 receives the state information transmitted from the sound output device 12, and outputs the state information to the state determining section 62.

In the next step S102, the state determining section 62 determines the wakefulness level of the driver 11, as described above, based on the state information, and outputs the wakefulness level information indicating the wakefulness level of the driver 11 to the transmitting section 64.

In the next step S104, the transmitting section 64 transmits the wakefulness level information to the sound output device 12, and the wakefulness level determining process then ends.

Figure 9:
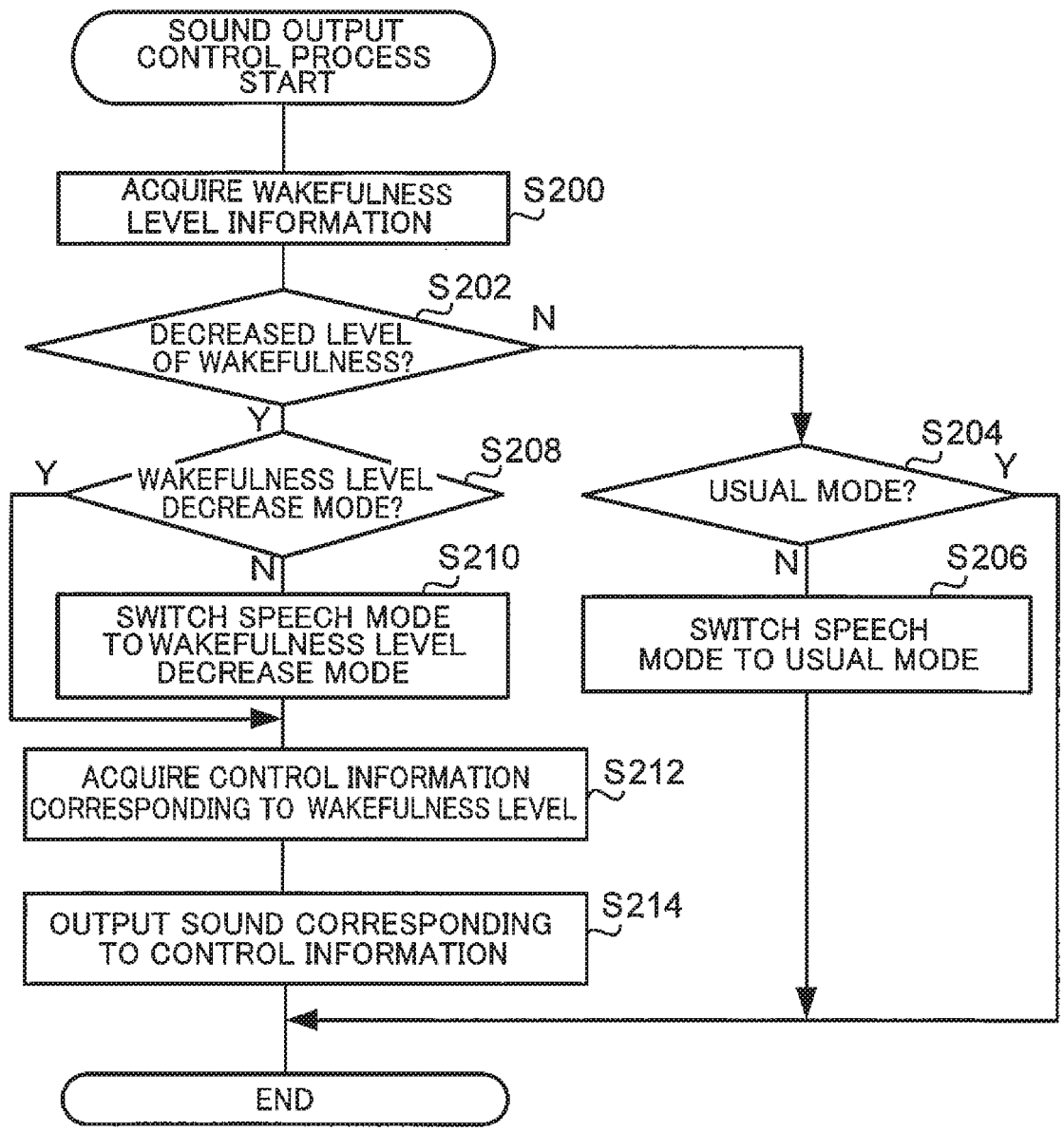
FIG. 9 is a flowchart showing a sound output control process executed by the sound output device according to the first exemplary embodiment.

When the sound output device 12 receives the wakefulness level information transmitted from the server 14 in this way, the sound output device 12 executes a sound output control process of controlling a sound output based on the wakefulness level of the driver 11 shown in FIG. 9. FIG. 9 is a flowchart showing an example of a flow of the sound output control process executed by the CPU 20 of the sound output device 12 according to the present exemplary embodiment. Further, in the present exemplary embodiment, the sound output control process shown in FIG. 9 is executed by the CPU 20 by executing the sound output control program 36 stored in advance in the storage section 32.

In step S200 shown in FIG. 9, the acquiring section 54 acquires wakefulness level decrease information received by the sound output device 12 from the server 14, and outputs the wakefulness level decrease information to the control section 50.

In the next step S202, the control section 50 determines whether or not the input wakefulness level decrease information indicates a state in which the wakefulness level of the driver 11 is decreased. In the present exemplary embodiment, as an example, in a case in which the wakefulness level indicated by the wakefulness level decrease information is "10", it is considered that the wakefulness level is not decreased, and in a case in which the wakefulness level decrease information is other than "10", in other words, in a case in which the wakefulness level is "9" or less, it is considered that the wakefulness level is decreased. For this reason, in the case in which the wakefulness level indicated by the wakefulness level decrease information is "10", a negative determination is made in step S202, and the process proceeds to step S204.

In step S204, the control section 50 determines whether or not the set speech mode is the usual mode. In a case in which the set speech mode is the usual mode, an affirmative determination is made in step S204, and the present sound output control process ends. On the other hand, in a case in which the set speech mode is not the usual mode, in other words, in a case in which the set speech mode is the wakefulness level decrease mode, a negative determination is made in step S204, and the process proceeds to step S206.

In step S206, the control section 50 switches the set speech mode from the wakefulness level decrease mode to the usual mode, and then ends the present sound output control process.

On the other hand, in the case in which the wakefulness level is other than "10", an affirmative determination is made in step S202, and the present sound output control process proceeds to step S208.

In step S208, the control section 50 determines whether or not the set speech mode is the wakefulness level decrease mode. In a case in which the set speech mode is the wakefulness level decrease mode, an affirmative determination is made in step S208, and the present sound output control process proceeds to step S212. On the other hand, in a case in which the set speech mode is not the wakefulness level decrease mode, in other words, in a case in which the set speech mode is the usual mode, a negative determination is made in step S208, and the present sound output control process proceeds to step S210.

In step S210, the control section 50 switches the set speech mode from the usual mode to the wakefulness level decrease mode.

In the next step S212, the control section 50 acquires control information corresponding to the wakefulness level indicated by the wakefulness level information from the control information DB 33. Further, in the present exemplary embodiment, the control section 50 acquires a specific content corresponding to a category number indicated by an item of a content of the control information. For example, in a case in which the wakefulness level is "8", the control section 50 acquires "every ×2 minutes" for the frequency, "1" for the tone, and "Category 2" for the content as the "control information" from the control information DB 33. Further, the control section 50 acquires the "pet" corresponding to Category 2 from the speech content DB 34.

In the next step S214, the control section 50 generates a sound (a speech) corresponding to the control information, outputs the generated sound by the output section 56, and then ends the present sound output control process. In the case in which the wakefulness level is "8" as in the example described above, the control section 50 generates a speech data for performing a speech of the content relating to the pet, sets the deviation degree of the tone to "2", and outputs the speech data to the output section 56 every ×2 minutes. Therefore, a speech of which the deviation degree of the tone is "2" is performed in relation to the pet to the driver 11 from the sound output device 12 every ×2 minutes.

As described above, in the sound output device 12 according to the present exemplary embodiment, the speech of the frequency, the tone, and the content corresponding to the decrease degree of the wakefulness level of the driver 11 is performed to stimulate the sympathetic nerve of the driver 11. Accordingly, the present exemplary embodiment may suppress a decrease in the wakefulness level of the driver 11.

Second Exemplary Embodiment

Hereinafter, a second exemplary embodiment will be described in detail. In the present exemplary embodiment, the same components and operations as those described in the first exemplary embodiment are denoted by the same reference numerals, and a detailed description thereof will be omitted.

The entire configuration of a sound output system 10 and a configuration of each of a sound output device 12 and a server 14 are the same as those of the first exemplary embodiment, and a description thereof will thus be omitted. Further, each of a state detecting process executed by the sound output device 12 and a wakefulness level determining process executed by the server 14 is the same as each of the state detecting process (see FIG. 7) and the wakefulness level determining process (see FIG. 8) according to the first exemplary embodiment, and a description thereof will thus be omitted.

In the present exemplary embodiment, some processes in a sound output control process executed by the sound output device 12 are different from those in the sound output control process (see FIG. 9) according to the first exemplary embodiment, and the sound output control process according to the present exemplary embodiment will be thus described with reference to FIG. 10.

FIG. 10 is a flowchart showing an example of a flow of the sound output control process executed by a CPU 20 according to the present exemplary embodiment. Since the sound output control process shown in FIG. 10 includes the same processes as those of the sound output control process according to the first exemplary embodiment shown in FIG. 9, the same processes will be denoted by the same reference numerals, and a detailed description thereof will be omitted.

As shown in FIG. 10, the sound output control process according to the present exemplary embodiment is different from the sound output control process according to the first exemplary embodiment in that, in a case in which an affirmative determination is made in step S208, a process of step S209 is performed before the sound output control process proceeds to step S212. That is, in the present exemplary embodiment, in a case in which a wakefulness level of a driver 11 is decreased and a wakefulness level decrease mode is set, the sound output control process proceeds from step S208 to step S209.

In step S209, a control section 50 increases a value indicating the wakefulness level based on an elapsed time after the wakefulness level decrease mode was set. In a case in which the wakefulness level of the driver 11 is difficult to increase and takes time, it is useful to further stimulate a sympathetic nerve of the driver 11 in order to rapidly increase the wakefulness level of the driver 11. Therefore, in the present exemplary embodiment, in a case in which a duration of the wakefulness level decrease mode is long (namely, in a case in which a decreased level of wakefulness is long) the control section 50 decreases the wakefulness level to be lower than a wakefulness level indicated by wakefulness level information, in order to further stimulate the sympathetic nerve of the driver 11. Specifically, the control section 50 subtracts the value indicating the wakefulness level acquired in step S200 by the number corresponding to the elapsed time. Note that a method of subtracting the value indicating the wakefulness level is not particularly limited, and for example, plural threshold values may be provided, and the value indicating the wakefulness level may be subtracted by "1" whenever the elapsed time is increased to exceed the threshold values.

Note that, in order to execute the present process, the control section 50 may acquire the elapsed time by setting a timer (not shown) when the wakefulness level decrease mode is set.

Therefore, in step S212 executed after step S209, the control section 50 acquires control information corresponding to the subtracted wakefulness level from a control information DB 33.

As described above, since the sympathetic nerve of the driver 11 can be more stimulated as a duration of the decreased level of wakefulness becomes longer, the present exemplary embodiment may rapidly increase the wakefulness level of the driver 11, for example, even in a case in which the wakefulness level of the driver 11 is difficult to be increased.

As described above, the sound output device according to each of the abovementioned exemplary embodiments includes: the acquiring section 54 that acquires the wakefulness level information indicating the degree of the wakefulness state of the driver 11 of the vehicle 13; and the control section 50 that controls the output section 56 to output the sound from the sound output section 31 based on at least one of a predetermined frequency, a predetermined tone, or a predetermined content for stimulating the sympathetic nerve of the driver 11, in a case in which the degree of the wakefulness state indicated by the wakefulness level information acquired by the acquiring section 54 is a degree indicating the decreased level of wakefulness.

As described above, in the sound output device 12 according to the above exemplary embodiments, since all of the frequency, the tone, and the content of the output speech (sound) stimulate the sympathetic nerve of the driver, who is a listener, stimulation of a sympathetic nerve of the driver 11 can be expected. Generally, in a state in which the sympathetic nerve is activated, the wakefulness level tends to become high. Therefore, the sound output device 12 according to each of the abovementioned exemplary embodiments may suppress the decrease in the wakefulness level of the driver 11.

Note that, in the above exemplary embodiments, a configuration in which the server 14 performs the wakefulness level determining process has been described. However, the wakefulness level determining process may also be performed in the sound output device 12.

Further, in the above exemplary embodiments, a configuration in which the speech of the content (topic) in which the interest degree is high is performed based on the wakefulness level of the driver 11 in order to stimulate the sympathetic nerve of the driver 11, has been described. However, the content of the speech for stimulating the sympathetic nerve of the driver 11 is not limited to such a form. For example, the content of the speech may be an advice for allowing the driver 11 to perform an action, or the like, for stimulating the sympathetic nerve. Specific examples of this case may include "How about drinking something?", "How about chewing gum?", "How about playing fun music?", and the like.

Further, in the above exemplary embodiments, a case in which each of the process performed by the CPU 20 and the process performed by the CPU 40 is a software process performed by executing the program, has been described. However, each of the process performed by the CPU 20 and the process performed by the CPU 40 may be a process performed by hardware. Further, each of the process performed by the CPU 20 and the process performed by the CPU 40 may be a process performed by combining software and hardware with each other. Further, each of the state detecting program 35 and the sound output control program 36 stored in the storage section 32 and the wakefulness level determining program 47 stored in the storage section 46 may be stored and distributed in various storage media.

Further, the disclosure is not limited to the abovementioned exemplary embodiments, and it goes without saying that various modifications can be made without departing from the spirit of the disclosure, Further to the abovementioned exemplary embodiments.

What is claimed is:

1. A vehicle sound output device comprising:
an acquiring section configured to acquire wakefulness level information that indicates a degree of a wakefulness state of a driver of a vehicle;
a database including a plurality of content based on monitored speech content of the driver, each content corresponding to a level of interest of the driver and to a degree of the wakefulness state of the driver; and
a control section configured to, in a case in which the degree of the wakefulness state indicates a decreased level of wakefulness, control a sound output section to output a sound based on a predetermined content that stimulates a sympathetic nerve of the driver, the predetermined content being selected from the plurality of content based on the level of interest of the driver and the degree of the wakefulness state of the driver in order to cause an interest degree of the driver to increase as the degree of the wakefulness state decreases,
wherein the sound output section outputs the sound as speech at a predetermined frequency that increases as the degree of the wakefulness state decreases, and at a predetermined tone that has a deviation degree that increases as the degree of the wakefulness state decreases, the predetermined tone includes one or more of a rhythm, tempo, and an intonation.

2. The vehicle sound output device according to claim 1, wherein the predetermined frequency increases as a duration of the decreased level of wakefulness increases.

3. The vehicle sound output device according to claim 1, wherein the predetermined tone has a deviation degree that increases as a duration of the decreased level of wakefulness increases.

4. The vehicle sound output device according to claim 1, wherein the predetermined content causes an interest degree of the driver to increase as a duration of the decreased level of wakefulness increases.

5. The vehicle sound output device according to claim 1, wherein the plurality of content is based on a count frequency of words in the monitored speech content of the driver.

6. The vehicle sound output device according to claim 5, wherein the words in the monitored speech content of the driver are associated with respective categories of topics.

7. The vehicle sound output device according to claim 5, wherein the plurality of content in the database is configured in a sequence based on the count frequency of words in the monitored speech content of the driver.

8. A sound output control method comprising:
acquiring wakefulness level information that indicates a degree of a wakefulness state of a driver of a vehicle; and
in a case in which the degree of the wakefulness state indicates a decreased level of wakefulness, controlling a sound output section to output a sound based on a predetermined content that stimulates a sympathetic nerve of the driver, the predetermined content being selected from a plurality of content stored in a database, the plurality of content based on monitored speech content of the driver, each content corresponding to a level of interest of the driver and to a degree of the wakefulness state of the driver, the predetermined content being selected from the plurality of content based on the level of interest of the driver and the degree of the wakefulness state of the driver in order to cause an interest degree of the driver to increase as the degree of the wakefulness state decreases,
wherein the sound output section outputs the sound as speech at a predetermined frequency that increases as the degree of the wakefulness state decreases, and at a predetermined tone that has a deviation degree that increases as the degree of the wakefulness state decreases, the predetermined tone includes one or more of a rhythm, tempo, and an intonation.

9. The sound output control method according to claim 8, wherein the plurality of content is based on a count frequency of words in the monitored speech content of the driver.

10. The sound output control method according to claim 9, wherein the words in the monitored speech content of the driver are associated with respective categories of topics.

11. The sound output control method according to claim 9, wherein the plurality of content in the database is configured in a sequence based on the count frequency of words in the monitored speech content of the driver.

12. A non-transitory computer readable medium storing a sound output control program causing a computer to execute a process, the process comprising:
acquiring wakefulness level information that indicates a degree of a wakefulness state of a driver of a vehicle; and
in a case in which the degree of the wakefulness state indicates a decreased level of wakefulness, controlling a sound output section to output a sound based on a predetermined content that stimulates a sympathetic nerve of the driver, the predetermined content being selected from a plurality of content stored in a database, the plurality of content based on monitored speech content of the driver, each content corresponding to a level of interest of the driver and to a degree of the wakefulness state of the driver, the predetermined content being selected from the plurality of content based on the level of interest of the driver and the degree of the wakefulness state of the driver in order to cause an interest degree of the driver to increase as the degree of the wakefulness state decreases,
wherein the sound output section outputs the sound as speech at a predetermined frequency that increases as the degree of the wakefulness state decreases, and at a predetermined tone that has a deviation degree that increases as the degree of the wakefulness state decreases, the predetermined tone includes one or more of a rhythm, tempo, and an intonation.

13. The non-transitory computer readable medium according to claim 12, wherein the plurality of content is based on a count frequency of words in the monitored speech content of the driver.

14. The non-transitory computer readable medium according to claim 13, wherein the words in the monitored speech content of the driver are associated with respective categories of topics.

15. The non-transitory computer readable medium according to claim 13, wherein the plurality of content in the database is configured in a sequence based on the count frequency of words in the monitored speech content of the driver.

\* \* \* \* \*